United States Patent [19]

Ison

[11] Patent Number: Plant 5,824

[45] Date of Patent: Dec. 9, 1986

[54] GRAPEVINE NAMED BLACK FRY

[76] Inventor: Bill Ison, Rte. 1, Brooks, Ga. 30205

[21] Appl. No.: 670,053

[22] Filed: Nov. 9, 1984

[51] Int. Cl.[4] ..... A01H 5/03
[52] U.S. Cl. ..... Plt./47
[58] Field of Search ..... Plt./47

*Primary Examiner*—R. E. Bagwill
*Attorney, Agent, or Firm*—Eugene T: Holmes

[57] ABSTRACT

A cross between the female variety Fry and the pollen parent variety Cowart, to produce an improved variety of muscadine grape.

1 Drawing Figure

DESCRIPTION OF THE VARIETY

A cross between the female variety Fry and the pollen parent variety Cowart.

The primary objective of the breeding was to produce an improved variety of muscadine plant; the fruit of which to have superior characteristics for fresh fruit than either of its parents. These characteristics to include high quality, 100% dry scar for longer shelf life; for fresh fruit, high sugar content; the plant to be vigorous and productive.

In comparison with both the seed and pollen parent, the new variety is similar in size to the seed parent; but resembles in color the pollen parent. The fruit of this new variety contains on the average of from 18.50 to 21.50 percent soluble solids, which sugar content is higher than the sugar content of the fruit of the pollen parent.

The present variety yields on the average of 5 to 8 tons per acre in tests conducted at Ison's Nursery & Vineyards, Brooks, Ga.

Asexual reproduction of the new variety either by soft wood cuttings or by layering as performed at Brooks, Ga. shows that the foregoing characteristics and distinctions come true to form and are established and transmitted through succeeding propagations.

The accompanying photograph shows a typical specimen of the vegetative growth and fruit of the new variety when the fruit is ripe and ready for picking and as depicted in color as nearly true as it is reasonably possible to make the same in color illustration of the characteristics.

The following is a detailed description of the new variety:

Species: *Vitis rotundefolia.*
Type: Vine.
Seed parent: Variety Fry.
Parent pollen: Variety Cowart.
Propagation: Holds its characteristics through succeeding propagation by either layering or by soft wood cuttings.
Locality where grown: Brooks, Ga.

Fruit borne: In clusters of approximately 8 to 15 berries per cluster.
Fruit size: Large, similar in size to the seed parent, or larger; diameter 1 3/16".
Fruit color: Greyed Purple Group 187A Fan 4 of The Royal Horticultural Society, London, England.
Sugar content: 18.50 to 21.50 percent soluble solids.
Fruit shape: Round.
Seed:
- *Average diameter.*—⅛ inch.
- *Average seed per berry.*—2.65.
- *Maturity date.*—Usually ripens about Sept. 21, at Brooks, Ga.

Pulp:
- A. *Color group fan.*—195A Fan 4 The Royal Horticultural Society, London, England.
- B. *Consistency.*—Medium soft, medium juicy as compared to most muscadine varieties.

Skin: Thick.
Foliage:
- *Leaf color.*—Fan 3 137A, The Royal Horticultural Society, London, England.
- *Leaf size and shape.*—Similar to most muscadine varieties.

Reproductive organs: Female.
Flowers: Imperfect, lacking functional stamens.
Growth habits: Vine requires support, vine vigorous and productive.
Canes: Medium to large calipers.
Diseases: Susceptible to Black Rot, tolerant to other diseases common to the muscadine.

This description was made from a muscadine vine grown at Ison's Nursery & Vineyards, Brooks, Ga.

DESCRIPTION OF THE DRAWING

There is attached hereto a permanently mounted color photograph accurately depicting the new plant and particularly the fruit and foliage thereof.

I claim:

1. The new and distinct variety of the specified plant as described and illustrated.

* * * * *

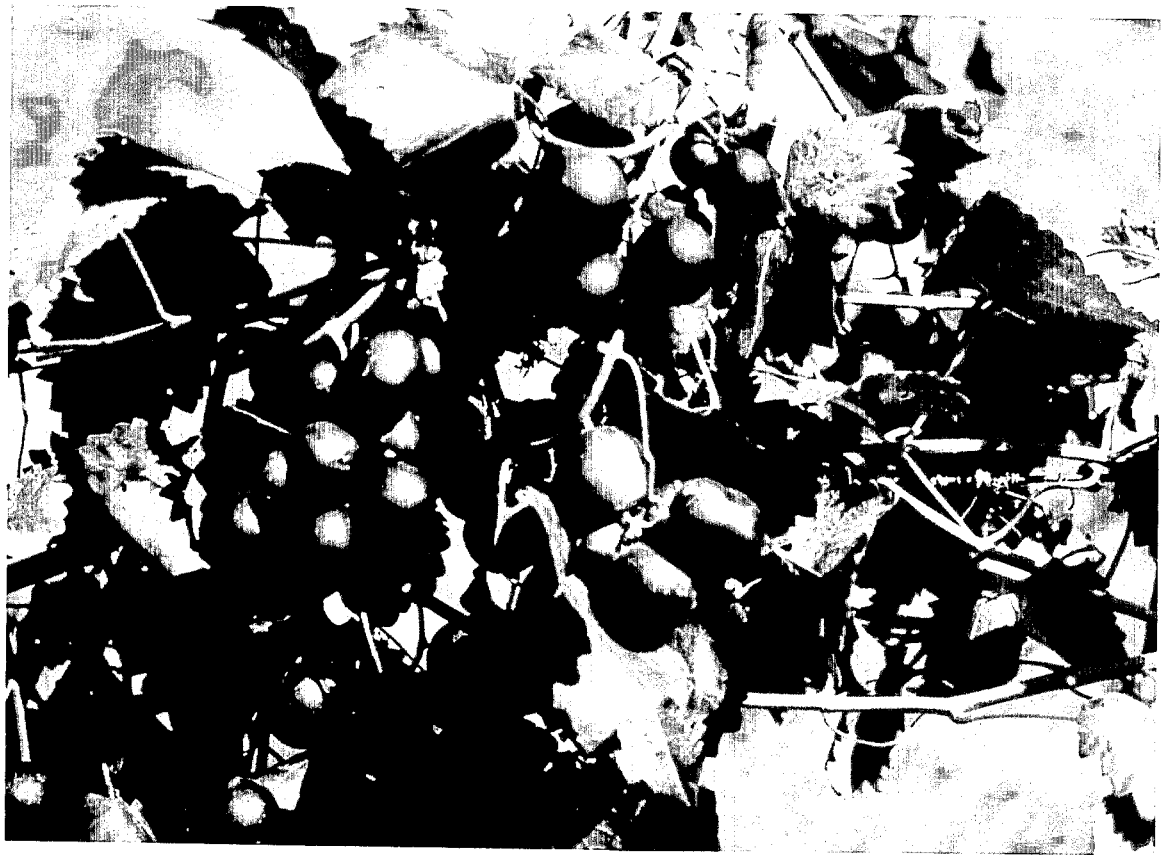

VARIETY "BLACK FRY"